United States Patent
Tracey

(10) Patent No.: US 12,104,722 B2
(45) Date of Patent: Oct. 1, 2024

(54) MEDIUM CONNECTOR

(71) Applicant: DEKA Products Limited Partnership, Manchester, NH (US)

(72) Inventor: Brian D. Tracey, Litchfield, NH (US)

(73) Assignee: Deka Products Limited Partnership, Manchester, NH (US)

(*) Notice: Subject to any disclaimer, the term of this patent is extended or adjusted under 35 U.S.C. 154(b) by 0 days.

(21) Appl. No.: 18/300,578

(22) Filed: Apr. 14, 2023

(65) Prior Publication Data
US 2023/0250904 A1  Aug. 10, 2023

Related U.S. Application Data

(63) Continuation of application No. 16/888,948, filed on Jun. 1, 2020, now Pat. No. 11,635,161, which is a continuation of application No. 14/263,379, filed on Apr. 28, 2014, now Pat. No. 10,704,714, which is a continuation of application No. 12/249,340, filed on Oct. 10, 2008, now Pat. No. 8,708,376.

(51) Int. Cl.
| | |
|---|---|
| F16L 21/08 | (2006.01) |
| A61M 39/10 | (2006.01) |
| F16L 21/00 | (2006.01) |
| F16L 37/02 | (2006.01) |
| F16L 37/098 | (2006.01) |

(52) U.S. Cl.
CPC ......... *F16L 21/08* (2013.01); *A61M 39/1011* (2013.01); *F16L 21/00* (2013.01); *F16L 37/02* (2013.01); *F16L 37/098* (2013.01); *F16L 37/0985* (2013.01); *A61M 2039/1027* (2013.01); *A61M 2039/1044* (2013.01); *Y10T 137/9029* (2015.04); *Y10T 137/9138* (2015.04)

(58) Field of Classification Search
CPC .................................. F16L 25/10; F16L 25/14
USPC .................................................. 285/9.2, 332.1
See application file for complete search history.

(56) References Cited

U.S. PATENT DOCUMENTS

| | | | |
|---|---|---|---|
| 3,881,961 A | 5/1975 | Nation | |
| 5,071,413 A * | 12/1991 | Utterberg | A61M 5/162 604/905 |
| 6,460,900 B1 * | 10/2002 | Bakke | E21B 17/20 285/330 |
| 2010/0005665 A1 | 1/2010 | Elliott et al. | |

\* cited by examiner

*Primary Examiner* — Aaron M Dunwoody
(74) *Attorney, Agent, or Firm* — Mark E. Tetreault

(57) ABSTRACT

A medium connector including a passage configured to allow for the flow of medium, and a multi-portion engagement surface positioned about the passage. The multi-portion engagement surface includes a first surface portion, and a second surface portion. The first surface portion is configured to provide an interference fit with a corresponding sealing surface of a mating connector. The second surface portion is configured to provide a clearance fit with the corresponding sealing surface of the mating connector. The ratio of the first surface portion and the second surface portion is selected to regulate an engagement force between the medium connector and the mating connector.

7 Claims, 5 Drawing Sheets

MEDIUM CONNECTOR

CROSS REFERENCE TO RELATED APPLICATIONS

This application is a continuation of U.S. Non-Provisional application Ser. No. 16/888,948, filed Jun. 1, 2020, which is a continuation of U.S. Non-Provisional application Ser. No. 14/263,379, filed Apr. 28, 2014, which is a continuation of U.S. Non-Provisional application Ser. No. 12/249,340, filed on Oct. 10, 2008, now U.S. Pat. No. 8,708,376, the entire disclosure of which is incorporated herein by reference.

TECHNICAL FIELD

This disclosure relates to medium connectors, and more particularly to medium connectors which may allow the engagement force between mating connectors to be regulated.

BACKGROUND OF THE DISCLOSURE

Medical device systems, such as medication delivery systems, frequently require various components to be fluidly connected to one another. For example, a syringe may be fluidly connected to an injection needle, an intravenous fluid supply bag may be fluidly connected to a catheter, etc. The fluid connections between the different components must be secure to prevent leakage as well as to prevent foreign substances, including air, from being introduced into the system. Additionally, it is often desirable to be able to quickly and easily make the desired connections without the user of tools One prevalent connection configuration in the medical device field is the Luer connection. Luer connections include cooperating male and female connector components having complimentary tapers. The taper geometry of Luer connectors are standardized as a continuous 6% taper. Connection between male and female Luer connectors may be made by pressing the male connector component into the female connector component. A friction fit is achieved between complimentary tapers of the connector components.

While Luer connectors provide reliable connection integrity and are relatively easy to use, no standardized tolerance is specified for the connector components. Slight deviations from an exact 6% taper may occur, e.g., as a result of manufacturing variation. Given that Luer connector components are often made of plastic materials, reliable connections are still achievable with connectors deviating slightly from the specified 6% taper, e.g., as a result of deformation of the plastic connector components and the relatively large contacting surface area. However, the depth of insertion of the connector components may vary as a result of any deviation from a 6% taper.

As such, when a defined insertion depth is required between the connector components, while a reliable connection may be achievable, the required insertion depth may not. The insertion depth of the connectors could be increased, e.g., by slightly deforming one or more of the connector components by pushing the connector components together more firmly. However, the constant taper of the connector components (resulting in an ever-increasing contact area), and the attendant engagement force, causes the insertion force to rapidly increase. It is possible that the engagement force may increase to a level that is greater than a force that is easily achievable by the user of the device, which may include elderly patients and/or patients having diminished physical capacity.

SUMMARY OF THE DISCLOSURE

According to a first implementation, a medium connector includes a passage configured to allow for the flow of medium, and a multi-portion engagement surface positioned about the passage. The multi-portion engagement surface includes a first surface portion, and a second surface portion. The first surface portion is configured to provide an interference fit with a corresponding sealing surface of a mating connector. The second surface portion is configured to provide a clearance fit with the corresponding sealing surface of the mating connector. The ratio of the first surface portion and the second surface portion is selected to regulate an engagement force between the medium connector and the mating connector.

One or more of the following features may be included. The mating connector may include a Luer taper connector. The multi-portion engagement surface may include a tapered surface, in which the first surface portion may have a first taper angle, and the second surface portion may have a second taper angle that is less than the first taper angle. Further, the second surface portion may be generally cylindrical. The multi-portion engagement surface may include a tapered surface, in which the first surface portion may have a first taper angle, and the second surface portion may have a second taper angle that is greater than the first taper angle. The second surface portion may include one or more recesses. The one or more recesses may include one or more radial slots. The one or more recesses may include one or more longitudinal slots.

The medium connector may include one or more retention features. The one or more retention features may include one or more snap-fit features.

According to another implementation, a medium connector includes a passage configured to allow for the flow of medium, and a tapered multi-portion engagement surface positioned about the passage. The multi-portion engagement surface includes a first surface portion, and a second surface portion. The first surface portion has a first taper angle configured to provide an interference fit with a corresponding sealing surface of a mating connector. The second surface portion has a second taper angle configured to provide a clearance fit with the corresponding sealing surface of the mating connector. The ratio of the first surface portion and the second surface portion is selected to regulate an engagement force between the medium connector and the mating connector.

One or more of the following features may be included. The mating connector may include a Luer taper connector. The second taper angle may be less that the first taper angle. The second surface portion may be generally cylindrical. The second taper angle may be greater than the first taper angle. The medium connector may include one or more retention features. The one or more retention features may include a snap fit feature.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF PREFERRED EMBODIMENTS

Figure 1A:
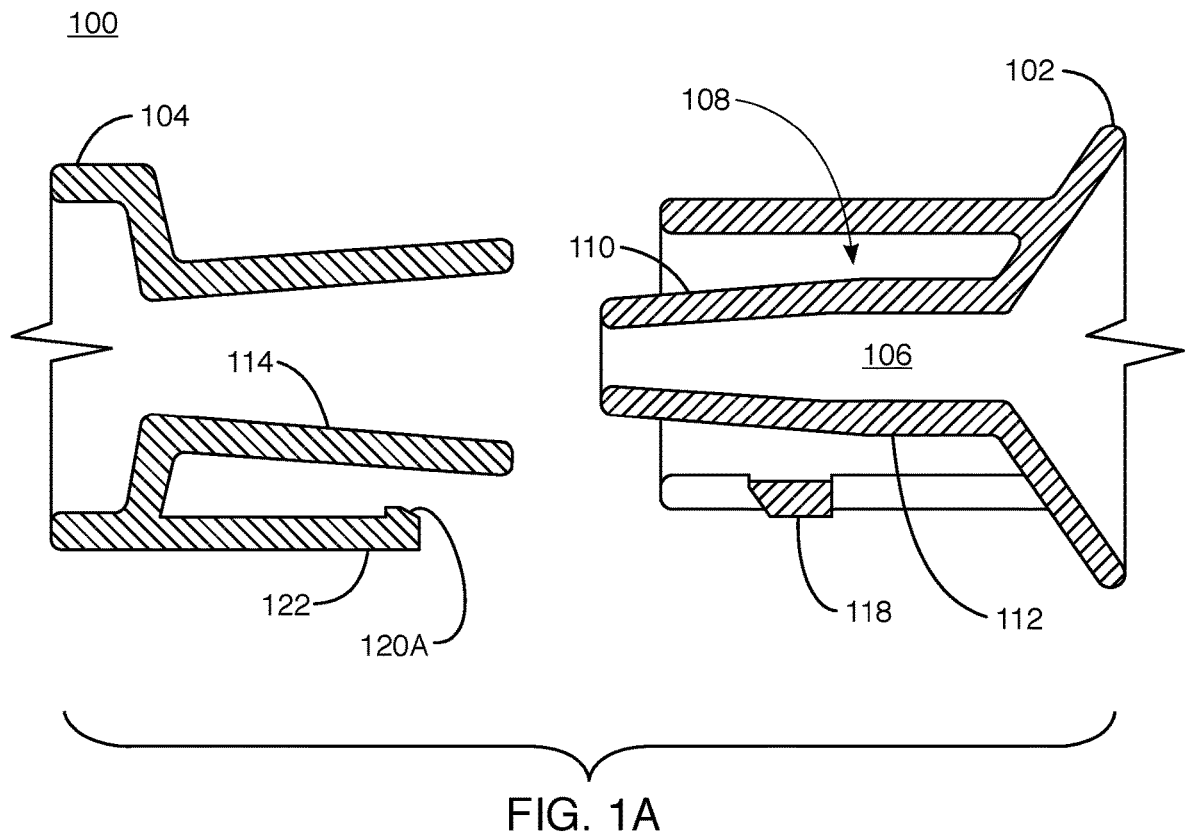
FIG. 1A diagrammatically depicts a first embodiment of a medium connector assembly, including a medium connector and a mating connector in a dis-engaged configuration.

Referring to FIG. 1A, there is shown a medium connector assembly 100 for connecting medium carrying components (not shown) and allowing the flow of medium therebetween. Examples of medium carrying components may include, but are not limited to, a delivery catheter and an insulin delivery pump, a fluid supply (such as an intravenous fluid supply bag, a dialysate supply, etc.) and a pump supply catheter, or the like. Connector assembly 100 may include medium connector 102 associated with a first medium carrying component (not shown) and mating connector 104 associated with a second medium carrying component.

Medium connector 102 may include passage 106 to allow for the flow of medium. The medium flowing between the medium carrying components, e.g., via passage 106, may include liquids (e.g., insulin, dialysate, saline solution, or the like), gases (e.g., air, oxygen, nitrogen, or the like), suspensions, or the like. Further, medium connector 102 may include multi-portion engagement surface 108, generally, positioned about passage 106. Multi-portion engagement surface 108 may include first surface portion 110, and second surface portion 112.

As will be discussed in greater detail below, first surface portion 110 of multi-portion engagement surface 108 may be configured to provide an interference fit with corresponding sealing surface 114 of mating connector 104. Further, second surface portion 112 of multi-portion engagement surface 108 may be configured to provide a clearance fit with corresponding sealing surface 114 of mating connector 104. The ratio of first surface portion 110 and second surface portion 112 may be selected to regulate an engagement between medium connector 102 and mating connector 104.

For example, corresponding sealing surface 114 of mating connector 104 may include a tapered surface, e.g., which may include a 6% taper (e.g., approximately 3.4 degree included taper) of a standard Luer taper connector (e.g., as defined by the ISO 594 standard). Of course, corresponding sealing surface 114 may include tapers other than a 6% Luer taper. Multi-portion engagement surface 108 may similarly include a tapered surface, in which first surface portion 110 may have a first taper angle, and second surface portion 112 may have a second taper angle that is less than the first taper angle. In one particular embodiment, the second taper angle may approach zero, such that second surface portion 112 may be generally cylindrical (e.g., may include a slight taper, such as a draft angle to facilitate manufacture). Of course, second surface portion 112 may include other, non-cylindrical, taper angles.

Figure 1B:
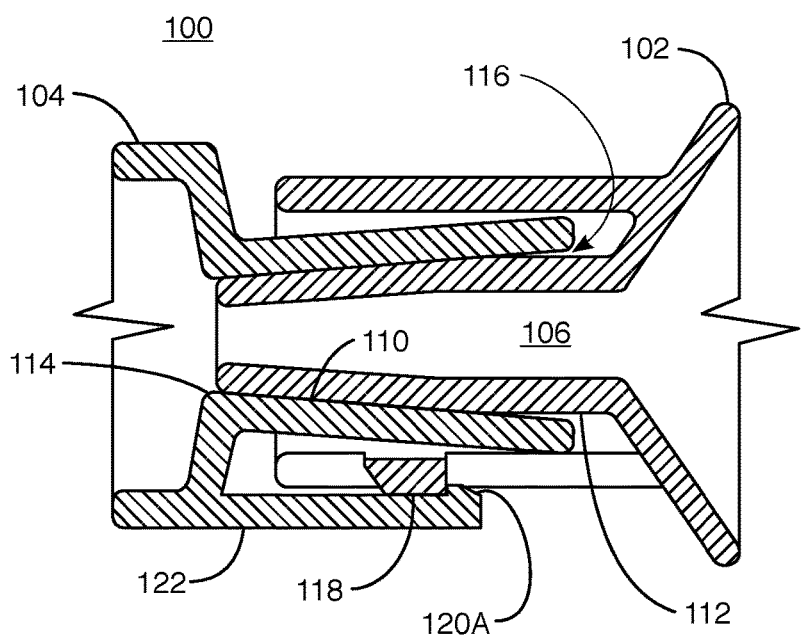
FIG. 1B diagrammatically depicts the first embodiment of the medium connector assembly of FIG. 1A in an engaged configuration.

Continuing with the above-stated example, first surface portion 110 of multi-portion engagement surface 108 may include a first taper angle corresponding to the angle of corresponding sealing surface 114 of mating connector 104 (e.g., a 6% taper). As shown in FIG. 1B, the corresponding taper of first surface portion 110 may provide an interference fit with corresponding sealing surface 114 of mating connector 104. As also shown, the second taper angle of second surface portion 112 may provide a clearance fit with corresponding sealing surface 114 of mating connector 104, e.g., which may result in at least partial clearance 116 between second surface portion 112 and corresponding sealing surface 114.

The contact surface area of medium connector 102 and mating connector 104 may remain generally constant once first surface portion 110 has engaged corresponding sealing surface 114. For example, as first surface portion 110 may be configured to provide an interference fit with corresponding sealing surface 114, while second surface portion 112 of multi-portion engagement surface 108 may be configured to provide a clearance fit with corresponding sealing surface 114, only first surface portion 110 may engage corresponding sealing surface 114.

Once first surface portion 110 engages corresponding sealing surface 114, further insertion of medium connector 102 relative to mating connector 104 may be attributable to the elastic and/or plastic deformation force of medium connector 102 in the region of first surface portion 110 and/or of mating connector 104 in the region of contact between corresponding sealing surface 114 and first surface portion 110 (e.g., as first surface portion 110 is forced into the progressively smaller opening provided by corresponding sealing surface 114), and the frictional interaction between first surface portion 110 and corresponding sealing surface 114 of mating connector 104.

As such, the ratio of first surface portion 110 and second surface portion 112 may be selected to regulate an engagement force between medium connector 102 and mating connector 104. As discussed above, second surface portion 112 may be configured to provide a clearance fit with corresponding sealing surface 114, and as such may not contribute to the engagement force (e.g., the insertion force per increment of axial insertion) between medium connector 102 and mating connector 104. Therefore, the ratio of first surface portion 110 to second surface portion 112 may be increased to increase the engagement force between medium connector 102 and mating connector 104. Conversely, the ratio of first surface portion 110 to second surface portion 112 may be decreased to decrease the engagement force between medium connector 102 and mating connector 104.

The ability to regulate the engagement force between medium connector 102 and mating connector 104 (e.g., based upon the ratio of first surface portion 110 and second surface portion 112) may allow the use of features associated with medium connector 102 (and/or the first associated medium carrying component) and/or mating connector 104 (and/or the second associated medium carrying component) which may require a minimum insertion depth to be achieved within a selected range of insertion forces. For example, medium connector 102 may include one or more retention features, e.g., which may facilitate a positive engagement and/or relative position between medium connector 102 and mating connector 104. As shown in FIGS. 1A and 1B, the one or more retention features may include one or more snap-fit features (e.g., cooperating snap-fit features 118, 120A, respectively associated with medium connector 102 and mating connector 104). As shown, one or more of cooperating snap-fit features 118, 120A may be disposed on a cantilever feature (e.g., cantilever arm 122), e.g., which may facilitate engagement/dis-engagement of cooperating snap fit features 118, 120A. Snap-fit features 118, 120A may require a minimum insertion depth to provide engagement therebetween. As described above, the ratio of first surface portion 110 and second surface portion 112 may be selected to regulate the engagement force between medium connector 102 and mating connector 104 associated with the insertion depth necessary to provide engagement between snap-fit features 118, 120A. While regulating the engagement force between the medium connector and the mating connector has been described in connection with the use of retention features, this is not intended as a limitation of the present disclosure, as the ability to regulate the engagement force between the medium connector and the mating connector may equally be used for other purposes.

Figure 2A:
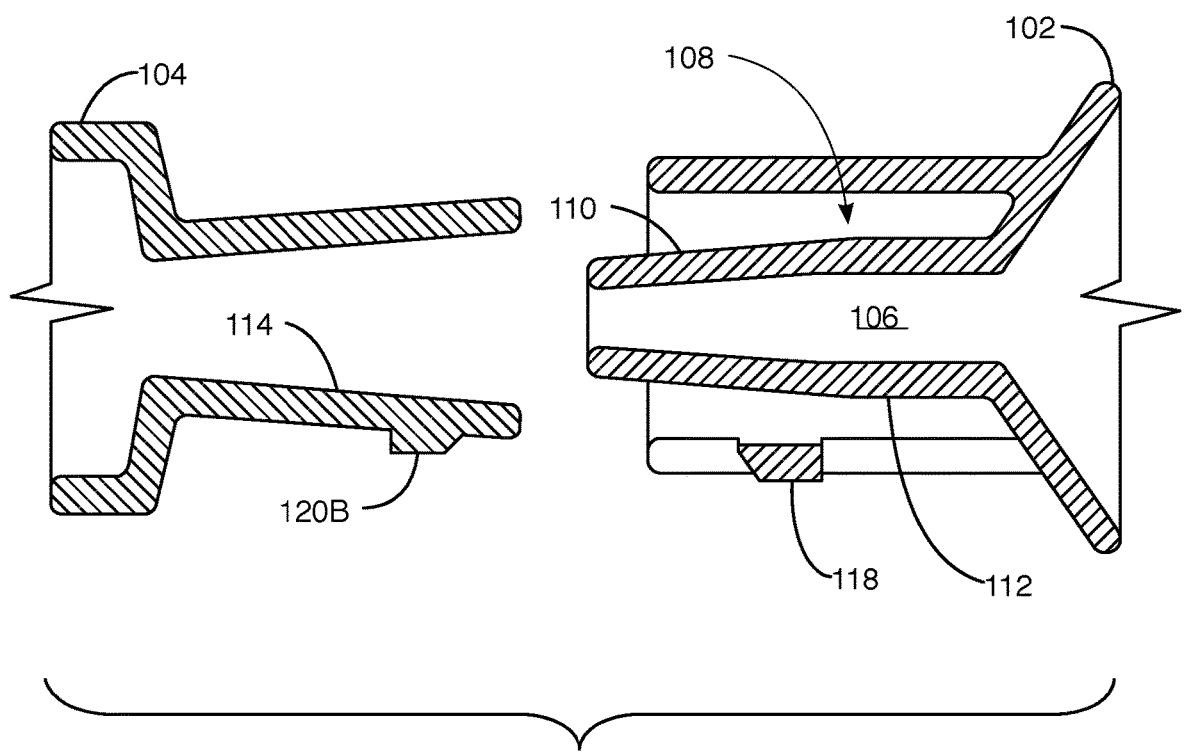
FIG. 2A diagrammatically depicts another embodiment of a medium connector assembly, including a medium connector and a mating connector in a dis-engaged configuration.
Figure 2B:
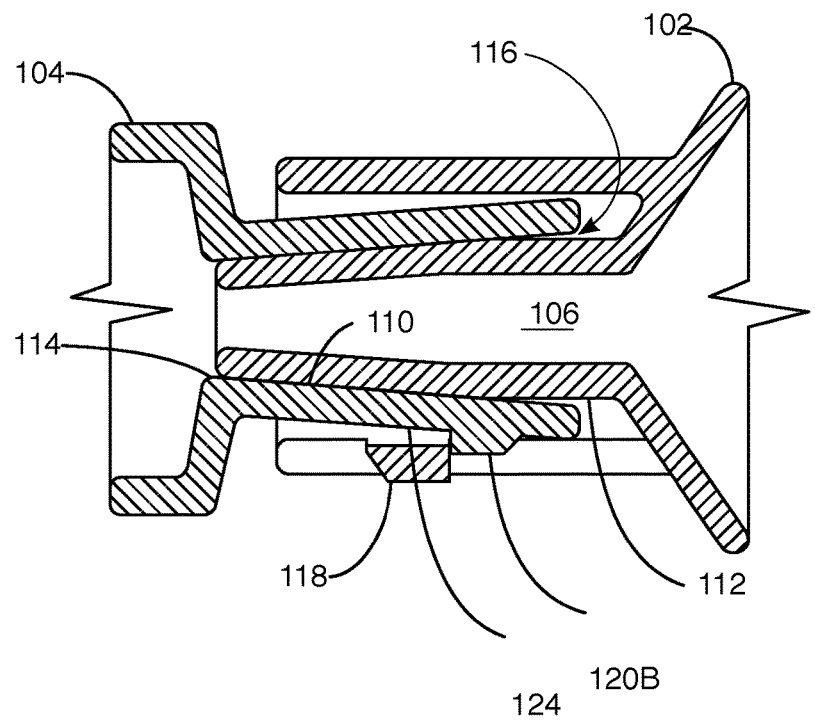
FIG. 2B diagrammatically depicts the medium connector assembly of FIG. 2A in an engaged configuration.

Referring also to FIGS. 2A and 2B, in a related embodiment, the medium connector assembly may include medium connector 102 associated with a first medium carrying component (not shown) and mating connector 104 associated with a second medium carrying component. As shown, one or more of the cooperating snap-fit features (e.g., cooperating snap-fit features 118, 120B) may be provided as a feature associated with one of the mating surfaces of the medium connector assembly (e.g., snap-fit feature 120b may be formed on member 124 defining corresponding sealing surface 114). Based upon, at least in part, the illustrated exemplary embodiments of FIGS. 1A-1B and 2A-2B, various additional/alternative arrangements may be readily understood, and are contemplated by the present disclosure.

Figure 3:
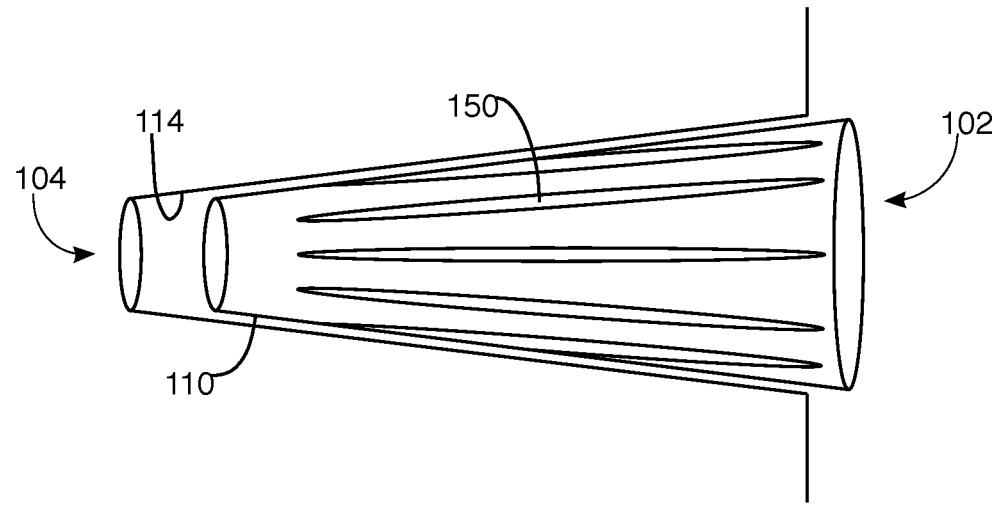
FIG. 3 diagrammatically depicts another embodiment of a medium connector assembly.

In addition/as an alternative to the second surface portion including a second taper angle, the second surface portion may include one or more recesses. For example, and referring also to FIG. 3, the second surface portion may include one or more recesses including one or more longitudinal slots (e.g., longitudinal slot 150), e.g., which may be formed in first surface portion 110. Longitudinal slot 150 may be configured to provide a clearance fit with cooperating sealing surface 114 of mating connector 104. For example, longitudinal slot 150 may provide a second surface portion which may not engage cooperating sealing surface 114 when first surface portion 110 is fully engaged with cooperating sealing surface 114 of mating connector 104. The ratio of first surface portion 110 and the radial slots (e.g., longitudinal slot 150) may be selected to regulate the engagement force between medium connector 102 and mating connector 104, e.g., in as much as longitudinal slot 150 may not provide a frictional engagement force with cooperating sealing surface 114 of mating connector 104.

Figure 4:
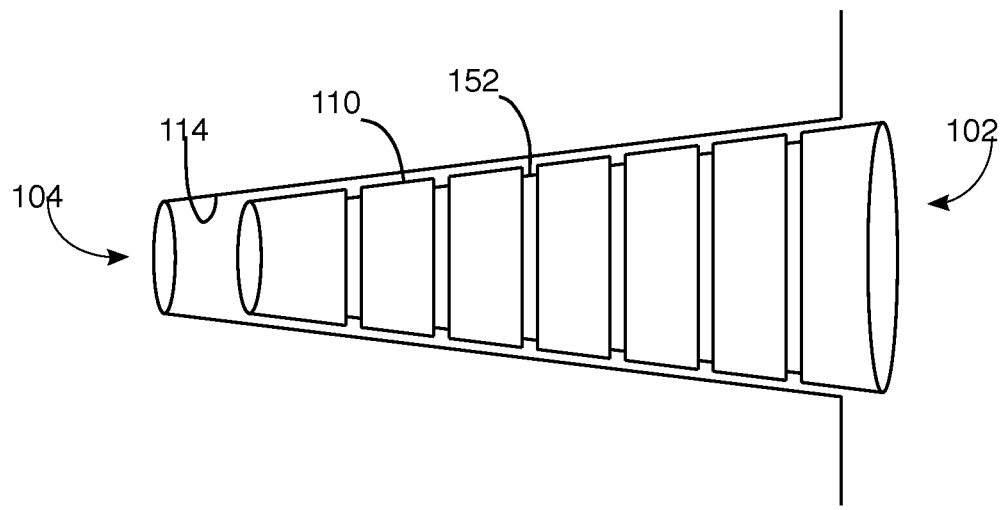
FIG. 4 diagrammatically depicts another embodiment of a medium connector assembly.

Referring also to FIG. 4, additionally/alternatively the second surface portion may include one or more recesses that may include one or more radial slots (e.g., radial slot 152). Similar to the above-described longitudinal slots (e.g., longitudinal slot 150), radial slot 152 may be configured to provide a clearance fit with corresponding sealing surface 114 of mating connector 104. As such, the ratio of first surface portion 110 and the radial slots (e.g., radial slot 152) may be selected to regulate the engagement force between medium connector 102 and mating connector 104. For example, radial slot 152 may not provide a frictional engagement force with cooperating sealing surface 114 of mating connector 104.

In addition to the specifically described and depicted recesses in the form of longitudinal slots and radial slots, the one or more recesses may include various additional and/or alternative configurations (e.g., dimples, etc.), which may be configured to provide a clearance fit with the cooperating sealing surface of the mating connector. As such, the ratio of the first surface portion and the second surface portion (including one or more recesses) may be selected to regulate an engagement force between the medium connector and the mating connector. Further, it will be appreciated that the number, arrangement, and character of the one or more recesses may vary according to design criteria and preference.

Figure 5:
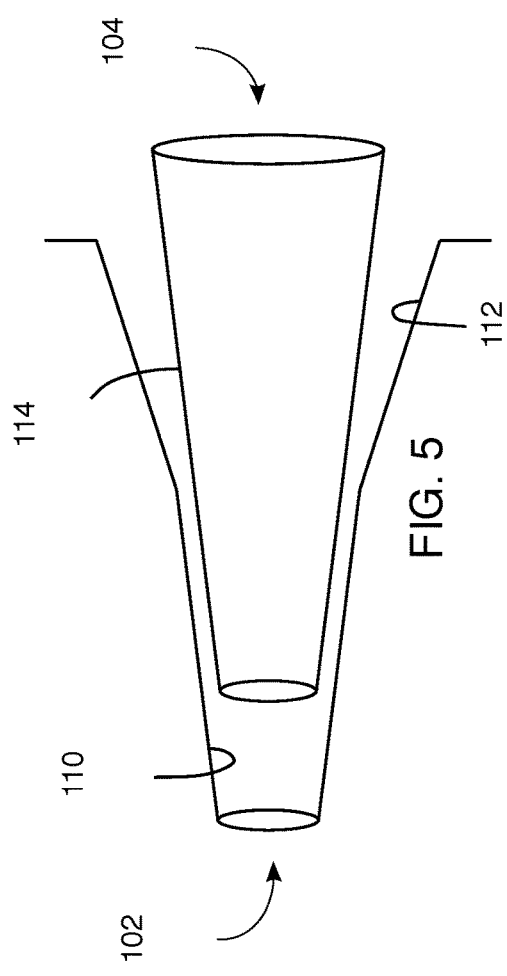
FIG. 5 diagrammatically depicts another embodiment of a medium connector assembly.
Figure 6A:
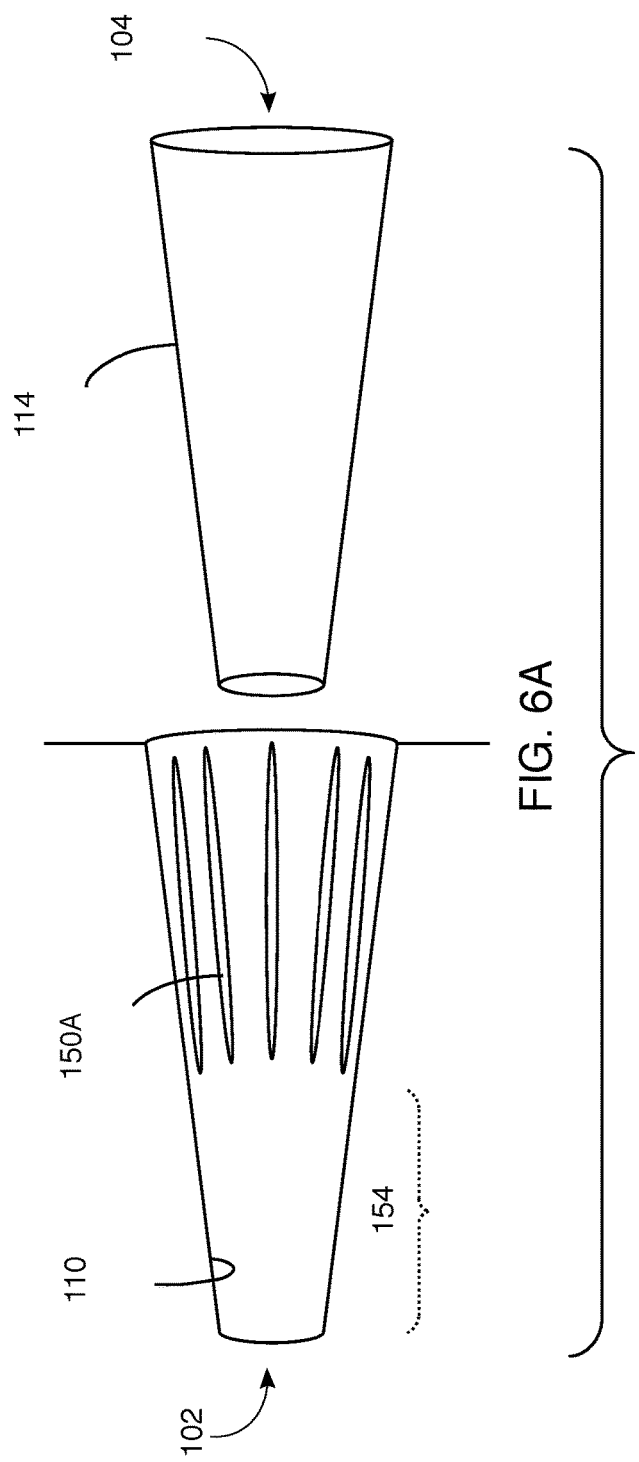
FIGS. 6A and 6B diagrammatically depict another embodiment of a medium connector assembly.
Figure 6B:
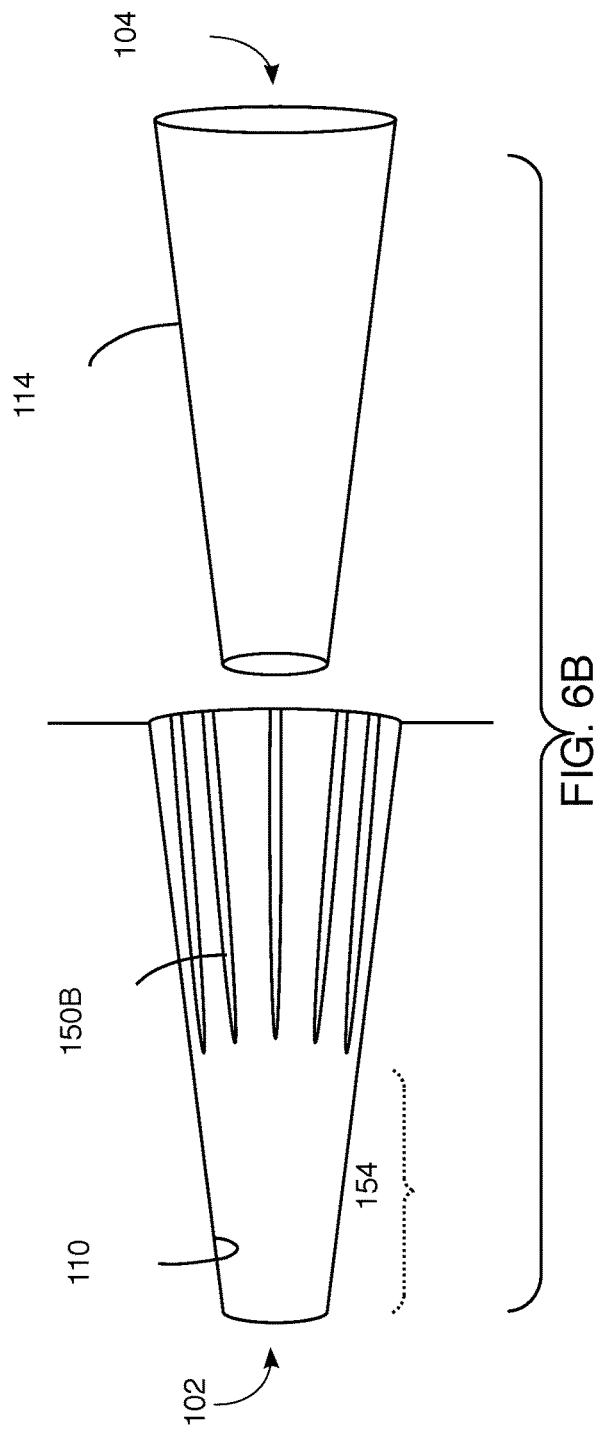
Figure 7:
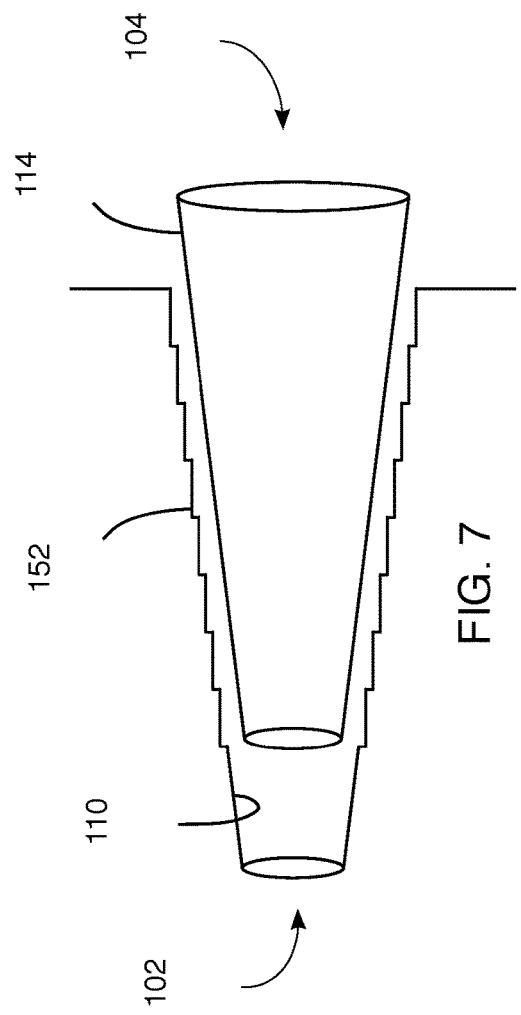
FIG. 7 diagrammatically depicts another embodiment of a medium connector.

While the above-described embodiments have been depicted having a multi-portion engagement surface configured as a male medium connector portion, referring also to FIGS. 5 through 7, medium connector 102 may additionally/alternatively be configured as a female connector portion. For example, medium connector 102 may include a female connector portion having a multi-portion engagement surface including first surface portion 110 and second surface portion 112. As shown in FIG. 5, the multi-portion engagement surface may include a tapered surface, in which first surface portion 110 may have a first taper angle configured to provide an interference fit with cooperating sealing surface 114 of male mating connector 104. Further, second surface portion 112 may have a second taper angle that is greater than the first taper angle. As such, second surface portion 112 may be configured to provide a clearance fit with cooperating sealing surface 114 of male mating connector 104.

Further, the second surface portion may include one or more recesses. For example, and referring also to FIGS. 6A and 6B, the one or more recesses may include one or more longitudinal slots (e.g., longitudinal slot 150A, 150B). Similar to previously described embodiments, first surface portion 110 may be configured to provide an interference fit with cooperating sealing surface 114 of male mating connector 104. Further, the second surface portion, including longitudinal slot 150A, 150B, may be configured to provide a clearance fit with cooperating sealing surface 114 of male mating connector 104. Medium connector 102 may include sealing region 154, which may not include longitudinal slots, e.g., to thereby facilitate achieving a seal between first surface portion 110 and cooperating sealing surface 114 of mating connector 104.

Referring also to FIG. 7, the second surface portion may include one or more recesses, in which the one or more recesses may include one or more radial slots (e.g., radial slot 152). Radial slot 152 may be configured to provide a clearance fit with cooperating sealing surface 114 of male mating connector 104.

In addition to the specifically described and depicted recesses in the form of longitudinal slots and radial slots, the one or more recesses may include various additional and/or alternative configurations (e.g., dimples, etc.), which may be configured to provide a clearance fit with the cooperating sealing surface of the mating connector. As such, the ratio of the first surface portion and the second surface portion (including one or more recesses) may be selected to regulate an engagement force between the medium connector and the mating connector. Further, it will be appreciated that the number, arrangement, and character of the one or more recesses may vary according to design criteria and preference.

A number of implementations have been described. Nevertheless, it will be understood that various modifications may be made. Accordingly, other implementations are within the scope of the following claims.

What is claimed is:

1. A connector combination, comprising:
   a mating connector having an interior passage, an interior surface of said interior passage forming a sealing surface; and
   a medium connector, comprising:
     a passage for the flow of medium;
     a first surface having a first taper angle;
     a second surface having a second taper angle;
     wherein the second taper angle is greater than the first taper angle;
   wherein the first surface is configured to engage with said sealing surface to form an interference fit,
   wherein the second surface is configured to provide a clearance fit with said sealing surface,
   a snap-fit feature on an exterior surface of said mating connector configured to engage with a cooperating snap-fit feature of said medium connector by flexing through said clearance fit;
   wherein said interference seal and engagement between said snap-fit feature and said cooperating snap-fit feature form a seal; and
   wherein a ratio of the first taper angle and the second taper angle regulates an engagement force between the medium connector and the mating connector.

2. The connector combination of claim 1, wherein the regulation of engagement force ensures that the medium connector engages the mating connector to create full engagement between the medium connector and the mating connector.

3. The connector combination of claim 1, wherein the second surface portion is generally cylindrical.

4. The connector combination of claim 1, wherein the second surface includes one or more recesses.

5. The connector combination of claim 4, wherein the one or more recesses include one or more radial slots.

6. The connector combination of claim 4, wherein the one or more recesses include one or more longitudinal slots.

7. The connector combination of claim 1, wherein the sealing surface has a continuous 6% taper.

* * * * *